(12) United States Patent
Carmeliet

(10) Patent No.: US 7,687,463 B2
(45) Date of Patent: *Mar. 30, 2010

(54) TREATMENT OF AMYOTROPHIC LATERAL SCLEROSIS

(75) Inventor: Peter Carmeliet, Blanden (BE)

(73) Assignees: Vlaams Interuniversitair Instituut voor Biotechnologie vzw, Zwijnaarde (BE); Life Sciences Research Partners vzw, Leuven (BE)

( * ) Notice: Subject to any disclaimer, the term of this patent is extended or adjusted under 35 U.S.C. 154(b) by 378 days.

This patent is subject to a terminal disclaimer.

(21) Appl. No.: 11/597,573

(22) PCT Filed: May 27, 2005

(86) PCT No.: PCT/EP2005/052430

§ 371 (c)(1),
(2), (4) Date: Aug. 2, 2007

(87) PCT Pub. No.: WO2005/117946

PCT Pub. Date: Dec. 15, 2005

(65) Prior Publication Data

US 2008/0279906 A1    Nov. 13, 2008

(30) Foreign Application Priority Data

May 27, 2004    (EP) .................................. 04102334

(51) Int. Cl.
A61K 38/18    (2006.01)
C07K 14/475    (2006.01)

(52) U.S. Cl. .............................. 514/12; 514/2; 530/399; 530/350

(58) Field of Classification Search ........................ None
See application file for complete search history.

(56) References Cited

U.S. PATENT DOCUMENTS

| 5,332,671 | A | 7/1994 | Ferrara et al. |
| 6,455,283 | B1 | 9/2002 | Ferrara et al. |
| 7,125,856 | B1 | 10/2006 | Isner |
| 7,226,908 | B2 | 6/2007 | Carmeliet |
| 7,592,314 | B2 | 9/2009 | Carmeliet |
| 2003/0105018 | A1 | 6/2003 | Carmeliet et al. |
| 2008/0032314 | A1 | 2/2008 | Cameliet |

FOREIGN PATENT DOCUMENTS

| WO | WO 98/31395 | 7/1998 |
| WO | WO 99/46364 | 9/1999 |
| WO | WO 99/47677 | 9/1999 |
| WO | WO 00/17371 | 3/2000 |
| WO | WO 00/62798 | 10/2000 |
| WO | WO 01/76620 | 10/2001 |

OTHER PUBLICATIONS

Zachary, I. (2005). Neuroprotective role of vascular endothelial growth factor: signalling mechanisms, biological function, and therapeutic potential. Neurosignals. 14:207-221.*
Sun et al., "VEGF-induced neuroprotection, neurogenesis, and angiogenesis after focal cerebral ischemia," Journal of Clinical Investigation, 2003, pp. 1843-1851, vol. 111, No. 12.
Greenberg et al., "VEGF and ALS: The luckiest growth factor?" Trends in Molecular Medicine, 2004, pp. 1-3, vol. 10, No. 1.
Storkebaum et al., "VEGF: A critical player in neurodegeneration," Journal of Clinical Investigation, 2004, pp. 14-18, vol. 113, No. 1.
Storkebaum et al., "VEGF: Once regarded as a specific angiogenic factor, now implicated in neuroprotection," Bioessays, 2004, pp. 943-954, vol. 26, No. 9.
PCT International Search Report, PCT/EP2005/052430, dated Sep. 7, 2005.
Airaksinen et al., The GDNF Family: Signalling, Biological Functions and Therapeutic Value, Nature Reviews Neuroscience, May 2002, pp. 383-394, vol. 3.
Andersen, Peter M., Genetics of sporadic ALS, ALS and other motor neuron disorders 2001, pp. S37-S41, vol. 2, Suppl. 1.
Autiero et al., Role of PlGF in the intra- and intermolecular cross talk between the VEGF receptors Flt1 and Flk1, Nature Medicine, Jul. 2003, pp. 936-943, vol. 9, No. 7.
Azzouz et al., VEGF delivery with retrogradely transported lentivector prolongs survival in a mouse ALS model, Nature, May 27, 2004, pp. 413-417, vol. 429.
Borasio et al., A placebo-controlled trail of insulin-like growth factor-1 in amyotrophic lateral sclerosis, Neurology, Aug. 1998, pp. 583-586, vol. 51.
Boyd et al., A dose-dependent facilitation and inhibition of peripheral nerve regeneration by brain-derived neurotrophic factor, European Journal of Neuroscience, 2002, pp. 613-626, vol. 15.
Cao et al., VEGF links hippocampal activity with neurogenesis, learning and memory, Nature Genetics, Aug. 2004, pp. 827-835, vol. 36, No. 8.
Carmeliet, Angiogenesis in health and disease, Nature Medicine, Jun. 2003, pp. 653-660, vol. 9, No. 6.
Caroni et al., Role of Muscle Insulin-like Growth Factors in Nerve Sprouting: Suppression of Terminal Sprouting in Paralyzed Muscle by IGF-binding Protein 4, The Journal of Cell Biology, 1994, pp. 893-902, vol. 125.
Chen et al., Abstract. Lack of association of VEGF promoter polymorphisms with sporadic ALS, Neurology, 2006, pp. 508-510, vol. 67, No. 3.
Cleveland et al., From Charcot to Lou Gehrig: Deciphering Selective Motor Neuron Death in ALS, Nature Reviews Neuroscience. Nov. 2001, pp. 806-819, vol. 2.

(Continued)

Primary Examiner—Christine J Saoud
Assistant Examiner—Jon M Lockard
(74) Attorney, Agent, or Firm—TraskBritt

(57) ABSTRACT

The present invention relates to the treatment of motoneuron diseases. More particularly the invention relates to the treatment of amyotrophic lateral sclerosis (ALS). It is found that the intracerebroventricular delivery of low amounts of vascular endothelial growth factor into a preclinical ALS animal model induces a significant motor performance and prolongation of survival time of said animals.

7 Claims, No Drawings

OTHER PUBLICATIONS

Del Bo et al., Vascular Endothelial Growth Factor Gene Variability is Associated with Increased Risk for AD, Annals of Neurology, Mar. 2005, vol. 57, No. 3.

Ernfors et al., Mice lacking brain-derived neurotrophic factor develop with sensory deficits, Nature, Mar. 10, 1994, pp. 147-150, vol. 368.

Ferrara et al., The biology of VEGF and its receptors, Nature Medicine, Jun. 2003, pp. 669-676, vol. 9, No. 6.

Friedlander, Robert M., M.D., Apoptosis and Caspases in Neurodegenerative Diseases, The New England Journal of Medicine, Apr. 3, 2003, pp. 1365-1375, vol. 348, No. 14.

Giess et al., Early Onset of Severe Familial Amyotrophic Lateral Sclerosis with a SOD-1 Mutation: Potential Impact of CNTF as a Candidate Modifier Gene, Am. J. Hum. Genet., 2002, pp. 1277-1286, vol. 70.

Giess et al., Potential role of LIF as a modifier gene in the pathogenesis of amyotrophic lateral sclerosis, Neurology, Feb. 22, 2000, p. 1003, vol. 54, No. 4.

Gurney, et al., Motor Neuron Degeneration in Mice That Express a Human Cu, Zn Superoxide Dismutase Mutation, Science, Jun. 17, 1994, pp. 1772-1775, vol. 264.

Howland et al., Focal loss of the glutamate transporter EAAT2 in a transgenic rat model of SODI mutant-mediated amyotropic lateral sclerosis (ALS), PNAS, Feb. 5, 2002, pp. 1604-1609, vol. 99, No. 3.

Jin et al., Abstract, Vascular Endothelial Growth Factor Rescues HN33 Neural Cells from Death Induced by Serum Withdrawal, Journal of Molecular Neuroscience, 2000, vol. 14.

Jin et al., Vascular endothelial growth factor (VEGF) stimulates neurogenesis in vitro and in vivo, PNAS, Sep. 3, 2002, pp. 11946-11950, vol. 99, No. 18.

Jin et al., Vascular enodthelial growth factor: Direct neuroprotective effect in in vitro ischemia, PNAS, Aug. 29, 2000, pp. 10242-10247, vol. 97, No. 18.

Kaspar et al., Retrograde Viral Delivery of IGF-1 Prolongs Survival in a Mouse ALS Model, Science, Aug. 8, 2003, pp. 839-842, vol. 31, No. 5634.

Kilpatrick et al., Abstract, Molecular mechanisms regulating motor neuron development and degeneration, Mol. Neurobiol., Jun. 1999, pp. 205-228, vol. 19, No. 3.

Koh, S. M., Ciliary Neurotrophic Factor Released by Corneal Endothelium Surviving Oxidative Stress Ex Vivo, IOVS, Sep. 2002, pp. 2887-2896, vol. 43, No. 9.

Krum et al., Angiogenic and Astroglial Responses to Vascular Endothelial Growth Factor Administration in Adult Rat Brain, Neuroscience, 2002, pp. 589-604, vol. 110, No. 4.

Kunst et al., Genetic Mapping of a Mouse Modifier Gene That Can Prevent ALS Onset, Genomics, 2000, pp. 181-189, vol. 70.

Lai et al., Effect of recombinant human insulin-like growth factor-1 on progression of ALS. Neurology, 1997, pp. 1621-1630, vol. 49.

Lambrechts et al., Abstract, VEGF: necessary to prevent motoneuron degeneration, sufficient to treat ALS? Trends in Molecular Medicine, Jun. 2004, pp. 275-282, vol. 10, No. 6.

Lambrechts et al., VEGF is a modifier of amyotrophic lateral sclerosis in mice and humans and protects motoneurons against ischemic death, Nature Genetics, Aug. 2003, pp. 383-394, vol. 34, No. 4.

Lino et al., Accumulation of SOD1 Mutants in Postnatal Motoneurons Does Not Cause Motoneuron Pathology or Motoneuron Disease, The Journal of Neuroscience, Jun. 15, 2002, pp. 4825-4832, vol. 22, No. 12.

Louissaint et al., Coordinated Interaction of Neurogenesis and Angiogenesis in the Adult Songbird Brain, Neuron, Jun. 13, 2002, pp. 945-960, vol. 34.

Luttun et al., Genetic dissection of tumor angiogenesis: are PIGF and VEGFR-1 novel anti-cancer targets, Biochimica et Biophysica Acta. 2004, pp. 79-94, vol. 1654.

Lutton et al., Revascularization of ischemic tissues by PIGF treatment and inhibition of tumor angiogenesis, arthritis and atherosclerosis by anti-Flt1, Nature Medicine, Aug. 2002, pp. 831-840, vol. 8, No. 8.

Marti et al., Systemic hypoxia changes the organ-specific distribution of vascular endothelial growth factor and its receptors, Proc. Natl. Acad. Sci., Dec. 1998, pp. 15809-15814, vol. 95, USA.

Masu et al., Disruption of the CNTF gene results in motor neuron degeneration, Nature, Sep. 2, 1993, pp. 27-32, vol. 365.

Miller et al., Riluzole for amyotropic lateral sclerosis (ALS)/motor neuron disease (MND), ALS and other motor neuron disorders 2003, pp. 191-206, vol. 4.

Miller et al., Targeted vectors for gene therapy, The FASEB Journal. Feb. 1995, pp. 190-199, vol. 9.

Miller G., Breaking Down Barriers, Science, Aug. 16, 2002, vol. 297, No. 5584.

Moore et al., Renal and neuronal abnormalities in mice lacking GDNF, Nature, Jul. 4, 1996, pp. 76-79, vol. 382.

Nagai et al., Rats Expressing Human Cytosolic Copper-Zinc Superoxide Dismutase Transgenes with Amyotropic Lateral Sclerosis: Associated Mutations Develop Motor Neuron Disease. The Journal of Neuroscience, Dec. 1, 2001, pp. 9246-9254, vol. 21, No. 23.

Ngo et al., Computational Complexity, Protein Structure Prediction, and the Levinthal Paradox, 1994, pp. 491-495.

Nutt et al., Randomized, double-blind trial of glial cell line-derived neurotrophic factor (GDNF) in PD. Neurology, Jan. 2003, pp. 69-73, vol. 60.

Ochs et al., A phase I/II trial of recombinant methionyl human brain derived neurotrophic factor administered by intrathecal infusion to patients with amyotrophic lateral sclerosis, ALS and other motor neuron disorders, 2000, pp. 201-206, vol. 1.

Pepper et al., Leukemia inhibitory factor (LIF) inhibits angiogenesis in vitro. Journal of Cell Science, 1995, pp. 73-83, vol. 108.

Pettit et al., The development of site-specific drug-delivery systems for protein and peptide biopharmaceuticals, TIBTECH, Aug. 1998, pp. 343-349, vol. 16.

Ramer et al., Glial cell line-derived neurotrophic factor increases calcitonin gene-related peptide immunoreactivity in sensory and motoneurons in vivo. European Journal of Neuroscience, 2003, pp. 2713-2721, vol. 18.

Raoul et al., ALS, IGF-1 and gene therapy: 'it's never too late to mend', Gene Therapy, 2004, pp. 429-430, vol. 11.

Rothstein, Jeffrey D., Of Mice and Men: Reconciling Preclinical ALS Mouse Studies and Human Clinical Trials, Apr. 2003, pp. 423-426, vol. 53, No. 4.

Ruprecht et al., Brain derived neurotrophic factor does not act on adult human cerebral endothelial cells, Neuroscience Letters, 2002, pp. 175-178, vol. 330.

Samii et al., Abstract, Vascular endothelial growth factor expression in peripheral nerves and dorsal root ganglia in diabetic neuropathy in rats, Neuroscience Letters, Mar. 12, 1999, pp. 159-162, vol. 262, No. 3, Elsevier Sci. Ireland Ltd., Ireland.

Sanchez et al., Renal agenesis and the absence of enteric neurons in mice lacking GDNF, Nature, Jul. 4, 1996, pp. 70-73, vol. 382.

Schratzberger et al. Favorable effect of VEGF gene transfer on ischemic peripheral neuropathy, Nat Med 6, 405-413 (2000).

Silverman et al., Abstract, Vascular. glial and neuronal effects of vascular endothelial growth factor in mesencephalic explants cultures, Neuroscience, 1999, pp. 1529-1541, vol. 90, No. 4.

Soker et al., Neuropilin-1 is Expressed by Endothelial and Tumor Cells as an Isoform-Specific Receptor for Vascular Endothelial Growth Factor, Cell 92, 735-745 (1998).

Sondell et al., Vascular Endothelial Growth Factor Has Neurotrophic Activity and Stimulates Axonal Outgrowth, Enhancing Cell Survival and Schwann Cell Proliferation in the Peripheral Nervous System, J Neurosci 19, 5731-5740 (1999).

Sopher et al., Androgen Receptor YAC Transgenic Mice Recapitulate SBMA Motor Neuronopathy and Implicate VEGF 164 in the Motor Neuron Degeneration. Neuron, Mar. 4, 2004, pp. 687-699, vol. 41.

Stockhammer, et al., Vascular endothelial growth factor in CSF: A biological marker for carcinomatous meningitis, Neurology, Apr. 25, 2000, pp. 1670-1676, vol. 54, No. 8.

Storkebaum et al., Treatment of motoneuron degeneration by intracerebroventricular delivery of VEGF in a rat model of ALS, Nature Neuroscience. Jan. 2005, pp. 85-92, vol. 8, No. 1.

Storment et al., Estrogen augments the vasodilatory effects of vascular endothelial growth factor in the uterine circulation of the rat, Am. J. Obstet. Gynecol., Aug. 2000. pp. 449-453, vol. 183, No. 2.

Strong et al. Amyotropic lateral sclerosis: A review of current concepts, ALS and other motor neuron disorders 2003, pp. 136-143, vol. 4.

Sun et al., VEGF-induced neuroprotection, neurogenesis, and angiogenesis after focal cerebral ischemia, The Journal of Clinical Investigation, Jun. 2003, pp. 1843-1851, vol. 111, No. 12.

Thorne et al., Delivery of Neurotropic Factors to the Central Nervous System, Clin Pharmacokinet 2001, pp. 907-946, vol. 40, No. 12.

Tsuzuki et al., Vascular Endothelial Growth Factor (VEGF) Modulation by Targeting Hypoxia-inducible Factor-1α→ Hypoxia Response Element→ VEGF Cascade Differentially Regulates Vascular Response and Growth Rate in Tumors, Cancer Research, Nov. 15, 2000, pp. 6248-6252, vol. 60.

Wang et al., VEGF overexpression induced post-ischaemic neuroprotection, but facilitates haemodynamic steal phenomena, Brain, 2005, pp. 52-63, vol. 128, No. 1.

Wells, J.A., Additivity of Mutational Effects in Proteins, Biochemistry, Sep. 18, 1990, pp. 8509-8517, vol. 29, No. 37.

Weston et al., Microarray analysis of VEGF-responsive genes in myometrial endothelial cells, Molecular Human Reproduction, 2002, pp. 855-863, vol. 8, No. 9.

Yamaguchi et al., Soluble Flt-1 (Soluble VEGFR-1), a Potent Natural Antiangiogenic Molecule in Mammals, Is Phylogenetically Conserved in Avians, Biochemical and Biophysical Research Communications, 2002, pp. 554-559, vol. 291.

Yang et al., Abstract. Co-accumulation of vascular endothelial growth factor with β-amyloid in the brain of patients with Alzheimer's disease, Neurobiology of Aging, Mar. 2004, pp. 283-290, vol. 25, No. 3.

Yasuhara et al., Neuroprotective effects of vascular endothelial growth factor (VEGF) upon dopaminergic neurons in a rat model of Parkinson's disease, European Journal of Neuroscience, 2004, pp. 1494-1504, vol. 19.

Office Action for U.S. Appl. No. 11/789,703 dated Apr. 17, 2009.

Office Action for U.S. Appl. No. 11/789,703 dated Dec. 15, 2008.

Office Action for U.S. Appl. No. 11/789,703 dated May 13, 2008.

* cited by examiner ively in >90% of cases without any family history. Although
TREATMENT OF AMYOTROPHIC LATERAL SCLEROSIS

FIELD OF THE INVENTION

The present invention relates to the treatment of motoneuron diseases. More particularly the invention relates to the treatment of amyotrophic lateral sclerosis (ALS). It is found that the intracerebroventricular delivery of low amounts of vascular endothelial growth factor into a pre-clinical ALS animal model induces a significant motor performance and prolongation of survival time of said animals.

INTRODUCTION TO THE INVENTION

Amyotrophic lateral sclerosis (ALS) is a devastating paralyzing disorder, killing patients within 3 to 5 years after onset[1-4]. Clinical symptoms primarily result from progressive degeneration of motoneurons in the spinal cord and brain stem, largely sparing cognitive performance. The disease affects healthy individuals in the midst of their life, sporadically in >90% of cases without any family history. Although more males than females are affected before the age of 60 years, both genders are similarly affected at older age[5]. With the ageing population, increasingly more individuals suffer ALS—the third most common neurodegenerative disorder[6]. Many ALS patients first notice muscle weakness in their limbs ("limb-onset" ALS). In ~25% of ALS patients, motoneurons first degenerate in the motor nuclei of the brain stem ("bulbar-onset" ALS), causing dysarthria, dysphagia and respiratory problems. Bulbar-onset ALS patients generally exhibit a faster and more aggressive disease progression than do limb-onset patients, but the latter eventually develop bulbar symptoms as well. The precise cause of motoneuron degeneration in most cases remains largely enigmatic[2,4,7]. SOD-1 mutations cause motoneuron degeneration in humans and, when overexpressed, also in transgenic mice. In fact, SOD-1$^{G93A}$ mice have become the gold standard animal model to assess the therapeutic potential of novel drug candidates[8]. SOD-1$^{G93A}$ rats develop an aggressive form of ALS, but have not been used yet for evaluation of novel treatments[9,10]. No approved, effective cure is available yet for ALS. Riluzole is the only approved drug in some but not all countries, but it has a marginal benefit on survival, is costly, not free of side-effects and, importantly, ineffective on bulbar symptoms[16]. As ALS results from degeneration of motoneurons, neurotrophic growth factors, such as brain-derived neurotrophic factor (BDNF), ciliary neurotrophic factor (CNTF), insulin-like growth factor (IGF)-1, leukemia-inhibitory factor (LIF), cardiotrophin (CT)-1 and hepatocyte growth factor (HGF) have long been considered as therapeutic candidates for ALS. Gene transfer of GDNF but especially of IGF-1, using a retrogradelly axon-transported viral vector, has been shown to prolong survival of SOD-1$^{G93A}$ mice[17,18]. Though clinical trials are underway[c], the clinical applicability of gene therapy for ALS remains to be established and concerns about its irreversible nature, risk for adverse chromosomal effects, poor control of transgene expression, and large production needs still remain to be overcome. Delivery of recombinant neurotrophic growth factors, instead, is therefore an attractive therapeutic strategy, as it offers flexible control of the dose and duration of the administered protein. However, intrathecal infusion of BDNF[19], intracerebroventricular delivery of GDNF[a] or systemic administration of BDNF[b] or CNTF[20] has, to date, not resulted in substantial clinical improvement in ALS patients, except for a 26% slowing of disease progression after IGF-1 delivery in one but not in another study[21,22].

At least part of the failure can be ascribed to the short half-life, immunogenicity, dose-dependent dual effect on neuronal survival versus apoptosis, undesired toxicity and limited ability to cross the blood-brain barrier after systemic delivery of these proteins[23-25]. Another possible reason may relate to the fact that several of these factors, even while promoting survival of acutely injured motoneurons when exogenously supplied, may not play such a critical role in the endogenous control of adult motoneuron survival in a chronic disease such as ALS. We recently discovered that low VEGF levels are redundant for motoneuron development but cause adult-onset ALS-like motoneuron degeneration in genetically modified mice (WO0176620) and increase the risk of sporadic and familial ALS in humans as well[13-15]. VEGF is a prototype angiogenic factor, implicated in vessel growth in health and disease[11,12]. To avoid immune problems and systemic side effects, to overcome the limited ability of VEGF to cross the blood-brain barrier, and to achieve maximal VEGF protein levels in the spinal cord parenchyma, we developed a strategy, never previously used to examine the therapeutic potential of a recombinant protein in preclinical ALS studies, i.e. to deliver, intracerebroventricularly, recombinant VEGF for prolonged periods using a transgenic SOD-1$^{G93A}$ rat model of ALS. Surprisingly, we have found that extremely low levels of VEGF not only significantly ameliorates motoric performance but also prolongs the survival time in a rat pre-clinical ALS model with an unexpected long time. The results show that low levels of VEGF can slow down the disease progression of patients suffering from ALS when administrated intracerebroventricularly.

[c]world wide web.hdlighthouse.org/research/genetherapy/updates/0052als.phtml.
[a]world wide web.mdausa.org/research/ct-alsglia.html.
[b]world wide web.alsa.org/news/news01280-1.cfm

DETAILED DESCRIPTION OF THE INVENTION

The present invention shows that intracerebroventricular (ICV) delivery of low amounts of VEGF delays onset, ameliorates motoric performance and prolongs survival of a rat strain suffering an aggressive form of ALS. This is the first study showing a significant therapeutic effect of a recombinant growth factor on the disease characteristics in a preclinical ALS model. Several recombinant growth factors with known neurotrophic activity, including BDNF, IGF-1, CNTF, LIF and GDNF have been evaluated in ALS patients or SOD1$^{G93A}$ mice, but not a single recombinant growth factor provided consistently a substantial benefit[19-22,35], therefore since the failure of previous clinical trials[19-22] administration of recombinant growth factors has lost much of its attraction. As we show here VEGF has direct effects on motoneurons in vivo. Although VEGF is known to affect various neuronal processes in vivo[15], it has never been established whether VEGF exerted its effects directly on neurons or indirectly through other cell types or via other molecular intermediates. Thus, VEGF has a pleiotropic spectrum of activities, which may have contributed to its remarkable therapeutic benefit in this invention.

The present invention indicates that VEGF can be used to manufacture a medicament for the treatment of motoneuron disorders and more specifically for the treatment of amyotrophic lateral sclerosis and amyotrophic lateral sclerosis-like diseases. In a particular embodiment the VEGF$_{165}$-isoform is used for the manufacture of a medicament for the treatment of motoneuron disorders and more specifically for the treatment of amyotrophic lateral sclerosis and amyotrophic lateral sclerosis-like diseases wherein said VEGF is continuously administered close to the place of onset.

VEGF$_{165}$ is a 165-amino acid protein which is typically referred to as human VEGF (hVEGF). VEGF is expressed in a variety of tissues as multiple homo-dimeric forms (121, 145, 165, 189, and 206 amino acids per monomer) resulting from alternative RNA splicing. VEGF$_{121}$ is a soluble mitogen that does not bind heparin; the longer forms of VEGF bind heparin with progressively higher affinity. The heparin-binding forms of VEGF can be cleaved in the carboxy terminus by plasmin to release a diffusible form(s) of VEGF. In addition several molecules structurally related to VEGF have also been identified recently, including placenta growth factor (PlGF), VEGF-B, VEGF-C, VEGF-D and VEGF-E. Ferrara and Davis-Smyth (1997) Endocr. Rev., Ogawa et al. (1998) J. Biological Chem. 273:31273-31281; Meyer et al. (1999) EMBO J., 18:363-374.

The terms 'pharmaceutical composition' or 'medicament' or 'use for the manufacture of a medicament to treat' relate to a composition comprising VEGF as described above and a pharmaceutically acceptable carrier or excipient (both terms can be used interchangeably) to treat motoneuron diseases as indicated above. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. In a particular embodiment the 'medicament' may be administered by a method close to the place of onset. Indeed, the spatial gradient of VEGF levels and therapeutic benefit indicates that, despite the significant CSF turnover, VEGF is deposited in close proximity to its injection site. This might offer novel opportunities to tailor VEGF therapy to the patients' needs. Indeed, individuals suffering ALS with bulbar onset can benefit more from ICV or intrathecal delivery of VEGF at the cervical level, while ALS patients with lumbar onset can benefit more from an intrathecal infusion of VEGF at the lumbar level. Generally, the medicament is administered so that VEGF, more particularly VEGF$_{165}$, is given at a dose between 0.01 µg/kg/day and 1.5 µg/kg/day, more preferably between 0.05 µg/kg/day and 1 µg/kg/day, most preferably between 0.2 µg/kg/day and 0.8 µg/kg/day. Preferably a continuous infusion is used and includes the continuous subcutaneous delivery via an osmotic minipump. In another embodiment VEGF$_{165}$ is used for the manufacture of a medicament to treat motoneuron disease wherein said VEGF$_{165}$ is continuously administered close to the place of onset at a dose within a range between 0.05 µg/kg/day and 1 µg/kg/day. In another embodiment VEGF$_{165}$ is used for the manufacture of a medicament to treat motoneuron disease wherein said VEGF is continuously administered close to the place of onset at a dose within a range between 0.2 µg/kg/day and 0.8 µg/kg/day.

In another embodiment said close to the onset administration is an intrathecal administration.

In another embodiment said close to the onset administration is an intracerebroventricular administration. It should also be clear that the administration of VEGF$_{165}$ is continuously administered close to the place of onset at a dose within a range between 0.01 µg/kg/day-1.4 µg/kg/day or 0.01 µg/kg/day-1.3 µg/kg/day or 0.01 µg/kg/day-1.2 µg/kg/day or 0.01 µg/kg/day-1.1 µg/kg/day or 0.01 µg/kg/day-1 µg/kg/day or 0.01 µg/kg/day-0.9 µg/kg/day or 0.01 µg/kg/day-0.8 µg/kg/day or 0.01 µg/kg/day-0.7 µg/kg/day or 0.01 µg/kg/day or 0.6 µg/kg/day or 0.01 µg/kg/day-0.5 µg/kg/day or 0.01-0.4 µg/kg/day or 0.01 µg/kg/day-0.3 µg/kg/day or 0.01 µg/kg/day-0.2 µg/kg/day or 0.01 µg/kg/day-0.1 µg/kg/day or 0.01 µg/kg/day-0.09 µg/kg/day or 0.01 µg/kg/day-0.08 µg/kg/day or 0.01 µg/kg/day-0.07 µg/kg/day or 0.01 µg/kg/day-0.06 µg/kg/day or 0.01 µg/kg/day-0.05 µg/kg/day or 0.01 µg/kg/day-0.04 µg/kg/day or 0.01 µg/kg/day-0.03 µg/kg/day. It should also be clear that the administration of VEGF$_{165}$ is continuously administered close to the place of onset at a dose within a range between 0.02 µg/kg/day-1.5 µg/kg/day or 0.03 µg/kg/day-1.5 µg/kg/day or 0.04 µg/kg/day/kg/day-1.5 µg/kg/day or 0.05 µg/kg/day-1.5 µg/kg/day or 0.06 µg/kg/day-1.5 µg/kg/day or 0.07 µg/kg/day-1.5 µg/kg/day or 0.08 µg/kg/day-1.5 µg/kg/day or 0.09 µg/kg/day-1.5 µg/kg/day or 0.1 µg/kg/day-1.5 µg/kg/day or 0.2 µg/kg/day-1.5 µg/kg/day or 0.3 µg/kg/day-1.5 µg/kg/day or 0.4 µg/kg/day-1.5 µg/kg/day or 0.5 µg/kg/day-1.5 µg/kg/day or 0.6 µg/kg/day-1.5 µg/kg/day or 0.7 µg/kg/day-1.5 µg/kg/day or 0.8 µg/kg/day-1.5 µg/kg/day or 0.9 µg/kg/day-1.5 µg/kg/day or 1 µg/kg/day-1.5 µg/kg/day or 1.1 µg/kg/day-1.5 µg/kg/day or 1.2 µg/kg/day-1.5 µg/kg/day or 1.3 µg/kg/day-1.5 µg/kg/day.

Thus in a particular embodiment the infusion with a composition comprising VEGF is intrathecal. Intrathecal administration can for example be performed by means of surgically implanting a pump and running a catheter to the spine.

To clarify the invention the term 'motoneuron disease' is explained below. Motoneuron disease is a group of diseases involving the degeneration of the anterior horn cells, nerves in the central nervous system that control muscle activity. This leads to gradual weakening and eventually wasting of the musculature (atrophy). Diseases of the motoneuron are classified according to upper motoneuron (UMN) and/or lower motoneuron (LMN) involvement. Upper motoneurons originate in the brain, in particular, the motor cortex, and they synapse either directly or indirectly onto lower motoneurons. Upper motoneurons are more accurately referred to as premotoneurons, and they are responsible for conveying descending commands for movement. Lower motoneurons are devisable into two categories: visceral and somatic motoneurons. Visceral motoneurons are autonomic pre-ganglionic neurons that regulate the activity of ganglionic neurons, which innervate glands, blood vessels, and smooth muscle. Somatic motoneurons innervate skeletal muscle and include first, anterior horn cells, which as the name implies, are located in the anterior horn of the spinal cord, and second, lower motoneurons located in the cranial nerve nuclei. Amyotrophic lateral sclerosis or ALS is the most frequent form (accounting for around 80% of all cases) of motoneuron disorders. ALS is known as Lou Gehrig's disease, named after the famous Yankee baseball player. The initial symptoms of ALS are weakness in the hands and legs and often fasciculation of the affected muscles. Whichever limbs are affected first, all four limbs are affected eventually. Damage to the upper motoneurons produces muscle weakness, spasticity and hyperactive deep tendon reflexes. Lower motoneuron damage produces muscle weakness with atrophy, fasciculations, flaccidity and decreased deep tendon reflexes. ALS has features of both upper and lower motoneurons of the cranial nerves, therefore symptoms are isolated to the head and neck. Some patients will also display UMN involvement of the cranial nerves and if this is the sole manifestation it is referred to as Pseudobulbar pulsy. Spinal muscular atrophy or progressive muscular atrophy is a motoneuron disease that does not involve the cranial nerves and is due to lower motoneuron degeneration. Shy-Drager syndrome is characterized by postural hypotension, incontinence, sweating, muscle rigidity and tremor, and by the loss of neurones from the thoracic nuclei in the spinal cord from which sympathetic fibres originate. Destructive lesions of the spinal cord result in the loss of anterior horn cells. This is seen in myelomeningocele and in syringomyelia, in which a large fluid-filled cyst forms in the centre of the cervical spinal cord.

The beneficial effect with VEGF relates to the fact that in the present invention this recombinant growth factor was delivered continuously and directly into the cerebrospinal fluid (CSF)—the availability of the larger SOD1$^{G93A}$ rat models of ALS was therefore instrumental. The biodistribution data show that VEGF, after ICV delivery, is rapidly diffusing from the CSF into the spinal cord parenchyma and thus capable of reaching the lower spinal motoneurons though we cannot exclude that some of the benefit may also have come from an effect on upper motoneurons. The close correlation between the biodistribution of VEGF (higher in brain stem than in the lumbar spinal cord) and its therapeutic effect shows that VEGF induced its greatest effect at sites where its levels were highest. As VEGF is cleared from the central nervous system beyond 3 hours (similar as other neurotrophins[38]), continuous delivery of VEGF likely contributed to the beneficial effect. Other reasons may relate to the general safety profile of ICV-administered VEGF (we could not observe any prominent adverse effects when using a therapeutic dose, which was 10-fold below the toxicity threshold) and the lack of an immune response (which might have otherwise induced neutralizing antibodies). An immune reaction did occur upon systemic delivery of VEGF and, likely, the negligible penetration of VEGF across the blood-brain barrier would be only overcome by administering systemically massive—likely toxic—amounts of VEGF.

ICV delivery may seem cumbersome at first sight, but is technically feasible and already operational for other chronic neurological indications[43]. The discomfort of a single surgical intervention to position the pump may, in fact, greatly outweigh the benefits of this route of administration (lack of systemic side effects and immune response; controllable administration). Our previous genetic data indicate that VEGF affects both sporadic and familial ALS[14]. While we only could use, in the present invention, an animal model of familial ALS, there is a good chance that VEGF will be also effective in sporadic cases of ALS. After all, VEGF has survival effects for various types of neurons, regardless of the sort of stress (hypoxia, excitotoxicity, serum deprivation, mutant SOD1-related toxicity, etc) and is thus an attractive candidate[15]. VEGF therapy appears to be safe and well tolerated for protracted time periods, without causing vascular side. Our findings extend previous observations that VEGF is known to have qualitatively distinct biological activities (vascular permeability, angiogenesis) at different concentrations[57]. Moreover, low VEGF levels only stimulate angiogenesis in ischemic/injured brain when delivered directly into the brain parenchyma, but not into the CSF[48,58].

EXAMPLES

1. Systemic Versus Intracerebroventricular Delivery of Recombinant VEGF

We first assessed via which route, i.e. systemic or intracerebroventricular, VEGF would be best administered. Safe and effective growth factor therapy of ALS requires that administration of the protein should not mount an immune response or induce systemic adverse effects, but result in sufficiently high, i.e. therapeutic, levels in the spinal cord parenchyma. Initial studies indicated that all commercially available recombinant human, rat or murine VEGF preparations, when administered intraperitoneally to mice at 1 μg every two days (a therapeutic dose to stimulate angiogenesis[37]), caused a strong immune response within 2 weeks. The best results were obtained when using in-house E. coli-produced murine VEGF, but even this preparation caused an immune response within 4 weeks, thereby precluding chronic systemic delivery of VEGF. In addition, VEGF is hydrophilic and has a molecular weight of 44 kDa and is thus unlikely to cross the blood-brain or blood-cerebrospinal fluid (CSF) barrier with an efficiency of more than 1% of the injected dose[38]. To obtain sufficient VEGF levels in the spinal cord parenchyma, excessive amounts of VEGF, likely inducing toxic systemic side effects, would therefore have to be administered. Furthermore, VEGF is trapped not only by heparan sulfate-rich extracellular matrix in tissues but also, in the plasma, by soluble Flt1 (sFlt1), i.e. the extracellular ligand-binding domain of VEGF receptor-1 (also termed Flt1)[39,40]. We detected, however, 5-fold higher soluble Flt1 levels in the serum than in the cerebrospinal fluid in mice (3,800±594 μg/ml versus 810±66 μg/ml; N=3; P<0.05). Thus, a larger fraction of VEGF would be trapped by sFlt1 and heparan sulfate-rich matrix, when administered systemically than intracerebroventricularly. Lastly, although VEGF levels are undetectable in the CSF[41], the choroid plexus is one of the few sites in the body, where VEGF remains constitutively expressed in the adult[42]. Because of all these reasons, we evaluated whether intracerebroventricular (ICV) delivery of VEGF would offer an alternative approach and optimized the necessary techniques for long-term ICV delivery of growth factors. As we previously determined that the VEGF$^{164}$ isoform (the human equivalent is VEGF$_{165}$) exhibits the optimal biological properties to stimulate motoneuron survival[13] (WO0176620), we used this isoform in the rest of our study. Since rats were used for all delivery experiments (see below), we cloned and expressed a rat VEGF$^{164}$ protein preparation, which was >99% pure and endotoxin-free.

2. Biodistribution of VEGF after Intracerebroventricular Delivery

Nothing is known about the pharmacokinetics of VEGF in the central nervous system after ICV delivery[38]. It is even unknown whether VEGF administered into the CSF would be capable of diffusing into the spinal cord parenchyma across the ependymal barrier. We therefore first determined the distribution pattern of $^{125}$I-VEGF after ICV delivery in healthy rats. At one hour after a bolus ICV injection, only 12% of the injected amount of $^{125}$I-VEGF was still present in the CSF, whereas 70% and 12% were recovered in the parenchyma of the brain and spinal cord, respectively, indicating that $^{125}$I-VEGF readily diffused from the CSF into the parenchyma. Thus, similar as for NGF, but unlike BDNF, the ependymal layer does not represent a barrier for VEGF to diffuse into the parenchyme[38]. When expressing the $^{125}$I-VEGF levels per gram tissue, $^{125}$I-VEGF levels were highest in the vicinity of the injection site and progressively declined in a rostro-caudal gradient along the spinal cord: $^{125}$I-VEGF levels in the bulbar/cervical, thoracal and lumbar spinal cord were 80%, 50% and 16%, respectively, of those in the brain. At 3 hours after injection, only 30% of the injected $^{125}$I-VEGF was present in the brain and spinal cord, while negligible amounts were detectable after 24 hours, when $^{125}$I-VEGF was recovered in the excretions, suggesting that VEGF was cleared into the venous and lymphatic systems, as documented for other growth factors[38]. Two conclusions can be drawn from these experiments. First, ICV-delivered VEGF rapidly diffuses from the CSF to neurons in the parenchyma, but is then cleared within 24 hours from the CSF. As motoneurons in ALS chronically require survival signals, VEGF should be delivered continuously. Second, after ICV delivery, VEGF is distributed in a rostro-caudal gradient—this can have consequences for affecting motoneuron survival in a similar spatial pattern.

3. Long-Term Intracerebroventricular Delivery of Recombinant VEGF

Although prolonged ICV delivery of GDNF for up to 8 months has been achieved in humans for other neurodegenerative disorders[43], this route has not been used to evaluate the therapeutic potential of recombinant growth factors in pre-clinical ALS models. To achieve long-term continuous and constant delivery of recombinant VEGF, we implanted osmotic minipumps subcutaneously on the backs of the animals and connected them to a catheter, which we stereotactically positioned in the lateral ventricle of the brain. While technically feasible to catheterize the lateral ventricle in mice, the catheters failed to remain fixed in the brain and became detached after several weeks, as the mice tried to remove them by scratching their head. In addition, the large size of the pump, relative to the body size (almost 30% of their body size), precluded reliable motor performance measurements. We therefore chose to implant pumps, delivering compounds for up to 4 weeks, in an SOD1$^{G93A}$ rat ALS model to assess the therapeutic potential of ICV delivery of recombinant VEGF protein. By replacing the pumps every 4 weeks, we succeeded in reproducibly delivering VEGF protein for more than 100 days without any adverse effects (see below). The correct position and patency of the catheters was checked in each rat at the time of dissection. Importantly, VEGF was still biologically active in binding its receptors, VEGF receptor-1 (also termed Flt1) and VEGF receptor-2 (Flk1), after being incorporated into the osmotic minipump in the animals for several weeks. Indeed, when retrieved from the pumps after three weeks, 89% and 68% of the residual VEGF in the pump still bound Flt1 and Flk1, respectively, indicating that the majority of the rVEGF$^{164}$ stored in the pumps was still active. As VEGF has never been administered to the central nervous system chronically (the longest duration was one week) and the effects of acute versus chronic administration of VEGF may differ, we carefully assessed whether a particular dose of VEGF would stimulate motoneuron survival without causing excessive blood vessel growth or leakage, even not after prolonged delivery for several months. Initial experiments revealed that rats receiving intracerebroventricularly a high dose of VEGF (e.g. 20 μg/kg/day) all died after a few days. At 2 μg/kg/day, 66% of the rats became ill after 3 to 4 weeks. While they were not paralyzed (the animals could still walk normally when pushed), they were generally apathic. Macroscopic inspection and histological analysis of the brain and spinal cord revealed additional vessel growth, ventricular dilatation, and redness and edema of the brain and spinal cord. A dose range between 0.2 μg/kg/day and 0.6 μg/kg/day was well tolerated by the rats, without inducing edema, leakage or excess vessel growth—even when administered chronically for more than 100 days. At this dose, VEGF levels in the CSF remained undetectable. SOD1$^{G93A/LSd}$ rats (SOD1$^{G93A}$ rats with low SOD1$^{G93A}$ expression on Sprague-Dawley background; see example 4) were treated with 0.6 μg VEGF/kg/day. At this dose, VEGF levels in the CSF remained undetectable, presumably because infused VEGF rapidly diffused into the spinal parenchyma. This is important, as only detectable VEGF levels have been associated with pathology[41]. We therefore used a dose of 0.6 μg VEGF/kg/day to treat SOD1$^{G93A}$ rats. This dose is, even after correction for the relative distribution volume of the entire body versus the brain/spinal cord, still 5-fold lower than a dose used for therapeutic angiogenesis[37]. Artificial cerebrospinal fluid (aCSF), infused as control, was also well tolerated for prolonged periods, indicating that the surgical procedures were safe. Another advantage of this low VEGF dose was that it did not induce an immune response. Indeed, no anti-VEGF antibodies were detectable in the peripheral blood or CSF of rats, not even after 100 days of delivery of a dose range of 0.2 μg/kg/day to 0.6 μg/kg/day of VEGF.

4. Effect of VEGF in a Rat Model of ALS

SOD1$^{G93A}$ rats have not been previously used for evaluating novel ALS treatment paradigms. We used SOD1$^{G93A/LSd}$ rats, generated by Nagai et al[10] ("L" refers to the low, e.g. 2-fold increased, SOD1$^{G93A}$ levels in this model) on a Sprague-Dawley background (Sd). Disease progression is very aggressive in this model, killing the animals within 10 days after disease onset[10]. SOD1$^{G93A/LSd}$ rats exhibited a large inter-litter variability in disease onset, ranging from 95 to 145 days. To reduce this variability, we used SOD1$^{G93A/LSd}$ littermates and analyzed the results in a paired manner (N=17 rats analyzed in 6 litter-pairs; see methods for details). Compared to control artificial CSF (aCSF), treatment of SOD1$^{G93A/LSd}$ rats with 0.6 μg VEGF/kg/day at 60 days of age significantly delayed disease onset, and improved motor performance and overall clinical outcome, regardless of the scoring method. For instance, VEGF-treated SOD1$^{G93A/LSd}$ rats remained generally active, mobile, attentive, and groomed their fur, at a time when aCSF-animals already showed signs of paralysis, and were progressively becoming immobile and cachectic. Control animals had more severe muscle atrophy than VEGF-treated rats. ICV delivery of VEGF delayed, by 10 days, the onset of limb paralysis, scored as dragging of a hindlimb or failure to use a forelimb during walking or righting (P<0.05). Using a laser-beam detection system[10], we identified the age at which rats were no longer capable of crossing equally spaced laser-beams in an "activity cage" at least 1,000 times per hour—a measure of their spontaneous walking behaviour. After VEGF delivery, rats remained spontaneously active at an older age (135±5 days, aCSF versus 146±8 days, VEGF; P<0.05). We also videotaped the rats and determined the time the rats spent exploring their cage and counted the frequency the rats reared themselves upon their hindlimbs as additional measures of their spontaneous activity. Before disease onset, i.e. at 110 days of age, both groups explored their cage as actively and reared themselves as frequently (P=NS). Four days after aCSF-rats showed the first signs of limb paralysis, VEGF-treated rats explored their cages longer and reared themselves more frequently than aCSF-treated animals (P<0.05). Finally, VEGF prolonged the survival of these ALS rats by 10 days (P<0.01). Thus, despite the very rapid disease progression and the large inter-litter variability of disease onset in this model, VEGF-treatment delayed onset, improved motor performance and prolonged survival of SOD1$^{G93A/LSd}$ rats without causing adverse effects.

5. Molecular Mechanism of the Neuroprotective Effect of VEGF

We further explored the mechanisms by which VEGF prolonged motoneuron survival in vivo. In vitro studies indicated that VEGF protects motoneurons against stress-induced cell death by binding VEGF receptor-2 (also termed Flk1)[13], but a direct neurotrophic activity of VEGF in vivo has never been demonstrated. To address the latter issue, we generated transgenic mice, using the Thy1.2 expression cassette to drive expression of murine Flk1 in postnatal neurons[45]. Compared to non-transgenic littermates, Thy-Flk1 mice expressed more Flk1 mRNA transcripts (copies Flk1/$10^3$ copies HPRT: 470±45 versus 50±5; N=3; P<0.05) and protein. Flk1 expression in non-transgenic littermates was detectable in blood vessels and, at a lower level, in large motoneurons. In contrast, in Thy-Flk1 mice, high Flk1 levels were present on large motoneurons in the ventral horn, in addition to its baseline expression in endothelial cells. Thy-Flk1 mice appeared healthy and fertile and were intercrossed with SOD1$^{G93A}$ mice. Notably, neuronal overexpression of Flk1 in SOD1$^{G93A}$ mice delayed onset of motor impairment by 23 days (N=8; P<0.001) and Thy1-Flk1:SOD1$^{G93A}$ mice performed better than SOD1$^{G93A}$ mice during 26 days (N=8; P<0.01). In addition, Thy1-Flk1:SOD1$^{G93A}$ mice survived 10 days longer than their SOD1$^{G93A}$ littermates (N=8, P<0.05). Thus, these genetic findings indicate that Flk1 on motoneurons transmits key survival signals of endogenous VEGF, thereby delaying premature motoneuron degeneration in ALS. Further evidence for a neuroprotective effect of Flk1 was provided by generating transgenic mice, using the same Thy1.2 expression cassette to drive neuronal expression of a dominant-negative Flk1, which impairs VEGF signaling (Flk1$^{DN}$). Thy-Flk1$^{DN}$ mice also expressed elevated levels of the Flk1$^{DN}$ transgene in motoneurons. At 3 months of age, Thy-Flk1$^{DN}$ mice were healthy and fertile, and had normal muscle strength, motor performance and numbers of motoneurons (SMI32$^+$ motoneurons/ventral horn: 31±4.4, wild type mice versus 29±1.2, Thy-Flk1$^{DN}$ mice; N=4; P=NS). To stress the motoneurons, the mice were housed, every other day for 30 days, in a chamber with 10% $O_2$. Chronic intermittent hypoxia upregulated VEGF levels in the spinal cord (pg VEGF/µg protein: 12±0.5, normoxia versus 22±1.4, hypoxia; N=5; P<0.05). Wild type mice tolerated the hypoxia without any problem and their grip strength even slightly increased. In contrast, Thy-Flk1$^{DN}$ mice lost 25% of their grip strength within one week after exposure to hypoxia and remained weaker for the rest of the experiment. Histological analysis revealed a marked gliosis in the gray matter of Thy-Flk1$^{DN}$ mice but not in wild type mice (GFAP$^+$ area/gray matter area in ventral horn: 0.13±0.45%, wild type versus 2.7±0.45%, Thy-Flk1$^{DN}$; N=3-5; P<0.05). Furthermore, motoneurons in Thy-Flk1$^{DN}$ but not in wild type mice accumulated phosphorylated neurofilament (SMI31$^+$ neurons/10 ventral horn sections: none in wild type versus 15.3±7.2 in Thy-Flk1$^{DN}$; N=3-5; P<0.05). These findings thus illustrate that Flk1 has a critical protective role in adult motoneuron maintenance in conditions of hypoxic stress.

Materials and Methods

1. Production of recombinant rat VEGF$_{164}$ (VEGF$_{164}$).

VEGF$_{164}$ cDNA amplified from a rat cDNA library was cloned into the pPICZαA secretion vector and expressed using the *Pichia pastoris* yeast expression system, according to the instructions of the manufacturer (Invitrogen, Carlsbad, Calif.). After overnight dialysis of the yeast-conditioned medium against 10 mM acetic acid (pH 5.5), VEGF was purified by sequential chromatography on phenyl Sepharose 6 Phast flow and heparin-agarose columns (both from Amersham Pharmacia Biotech). The VEGF concentration was determined using the rat Duoset ELISA (R&D Systems, Abingdon, UK). The purified VEGF$_{164}$ was then electrophoresed and single 45 kDa or 22 kDa-stained bands under non-reducing and reducing conditions, respectively, were visualized by coomassie blue- and silver-staining of the gels. The band was confirmed to be recombinant rat VEGF$_{164}$ by immunoblotting with a monoclonal antibody specific for rVEGF$_{164}$ (R&D Systems) and N-terminal sequencing after Edman's degradation protocol. After trypsin digestion of the prominent 45 kDa band, which was followed by separation of the cleaved peptides on dHPLC, 3 internal peptides were selected and N-terminally sequenced according to Edman's degradation protocol. All three peptides were a perfect match to the published VEGF164 amino acid sequence.

2. Functional Characterization of VEGF$_{164}$

Binding of our VEGF$_{164}$ preparation to immobilized rhFc-FLT1 and rhFc-FLK1 (R&D Systems) receptors was compared with that of commercially available rat VEGF$_{164}$. Bound VEGF$_{164}$ was detected using biotinylated anti-rat VEGF antibodies (R&D Systems; 200 ng/ml), the ABC vector staining kit and photospectrometric readout. Home-made VEGF$_{164}$ exhibited a higher affinity towards rhFc-FLK1 and a similar binding affinity towards rhFc-FLT1. Endotoxin levels were determined by using the *Limulus Amebocyte* Lysate (LAL) kit (Bio-Whittaker, Walkersville, USA) and revealed the presence of 1 endotoxin unit per 350 µg VEGF$_{164}$ (or 3 E10-3 endotoxin unit per µg VEGF$_{164}$).

3. Radio-Labeled Experiments

Radio-labeled human $^{125}$I-VEGF was purchased from Amersham Pharmacia with a specific activity of 25 µCi/µg VEGF$_{165}$. 100 ng of this preparation was dissolved in 10 µL and stereotactically injected into the left lateral ventricle of healthy female Wistar rats by using a 33 Gauge Hamilton needle—stereotactic coordinates were the same as for the implantation of the osmotic pump (see below). Subsequent to ICV-injection, rats were dissected after 1, 3 and 24 hours, and the brain, spinal cord (divided into cervical, thoracal and lumbal spinal cord), blood and other organs (liver, intestine, heart, etc) weighed and the total counts per minute (cpm) measured using a gamma-counter. The distribution of $^{125}$I-hVEGF$_{165}$ in the parenchyma of the brain was evaluated by microautoradiography. First, cryosections of the brain and spinal cord, containing $^{125}$I-labeled VEGF$_{165}$ were dipped into photographic emulsion (Kodak, Cedex, France). After two days of exposure, the emulsified sections were developed and the location of silver grains, as detected by light microscopy, was used to determine the tissue distribution of the $^{125}$I-labeled VEGF$_{165}$.

4. Generation and Characterization of Transgenic Mice

Transgenic mice expressing Flk-1 specifically in adult neurons were generated using the mouse Thy1.2 expression cassette, as previously described 59. Murine Flk-1 cDNA was cloned into the Thy-1.2 expression cassette, and the linearized construct was microinjected into FvB mouse embryos using standard microinjection techniques. Founders were identified using PCR and expression of the transgene was determined by RT-PCR, Western blotting and immunostaining, as previously described[13,37].

5. Animals

Sprague-Dawley rats expressing the human SOD1$^{G93A}$ transgene (SOD1$^{G93A}$-L) were kindly provided by Dr. Itoyama[10], while mice expressing the human SOD1$^{G93A}$ transgene were backcrossed for more than 10 generations on a FvB background and were kindly provided by Dr. C. Kunst[60]. All experiments on animals were approved by the local animal ethics committee.

6. Surgical Procedures

To infuse recombinant rat VEGF$_{164}$ into the cerebral ventricle of the rats, Alzet osmotic pumps (model 2004) connected with a catheter to a brain infusion cannula were used. The brain infusion assembly was filled with 200 µl of a 5

µg/ml recombinant rat $VEGF_{164}$ solution or with artificial CSF, and primed during 48 h in saline. The composition of the artificial CSF was 150 mM $Na^+$, 3 mM $K^+$, 1.4 mM $Ca^{2+}$, 0.8 mM $Mg^{2+}$, 1 mM $PO_4^{3-}$, 155 mM $Cl^-$. For the implantation of the pumps, rats were anesthetized with halothane, a midline sagittal incision was made starting slightly behind the eyes, and the skull was exposed. A subcutaneous pocket in the midscapular area of the back of the rat was prepared, and the osmotic pump was inserted into the pocket. A hole was drilled through the skull, and the cannula placed using the following stereotaxic coordinates: 0.8 mm posterior to bregma, 1.6 mm lateral, and 4.5 mm ventral from skull surface. When the implantation procedure was completed, the skin incision was sutured, and the rat allowed to recover. After 28 days, the emptied osmotic pumps were replaced by a fresh, fully loaded and primed osmotic pump. To do so, the rat was anesthetized again and a small skin incision in the midscapular region of the back was made. The catheter was cut 5 mm anterior to the spent pump, and a fresh pump was attached to the catheter tubing. This procedure results in a continuous infusion of $VEGF_{164}$, at a rate of 0.25 µl/h (corresponding to 1.25 ng VEGF/hour) into the CSF. In a prevention trial, pumps were implanted at the age of 60 days, and in a regression trial, pumps were implanted at 80 days (age of disease onset). Mice were exposed to chronic intermittent hypoxia by transferring them, every other day during 30 days, to an oxygen chamber, containing 12% oxygen.

7. Behavioural Analysis

Three times a week, motor performance of the rats was tested using rotarod, dynamometer, and spontaneous activity measurements. A rotarod for rats (Ugo Basile, Comerio VA, Italy) with a constant rotation speed (15 rotations per minute) was used. The average of 5 trials of maximum 180 seconds was determined on a given day. When the average time a rat could stay on the rotarod was less than 120 seconds, this was considered a failure. For the dynamometer test, an average of 5 trials was made for each rat, and when the rat was unable to pull on average 800 mg, this was considered a failure. To quantify spontaneous activity, rats were placed for 3 hours into an activity cage (Ugo Basile), and the average activity per hour, i.e. the number of times the rat crossed an infrared beam positioned 10 cm above the cage floor, was calculated. As a criterion to score the age of disease onset of the rats, dragging of one limb during walking was used. In previous studies, failure of the animal to right itself after being turned on either side for a maximum of 30 seconds was scored as "clinical death"[9]. However, initial experiments revealed that $SOD1^{G93A}$ rats, unable to right themselves, could still survive for several days—this was particularly the case for rats with forelimb disease. We therefore scored the time of death as the day the rats had lost 40% of their original body weight at the last presymptomatic age, as experiments indicated that the animals within 24-36 hours thereafter. The data generated by the described clinical tests and the survival data were analyzed using Kaplan Meyer statistical analysis or by using ANOVA repeated measures (rotarod, dynamometer and activity).

8. Histology, Immunohistochemistry and ELISAs

Animals were perfused transcardially, under deep Nembutal anaesthesia, with 0.9% NaCl solution followed by 1% phosphate buffered paraformaldehyde. Spinal cord and brain were dissected, post-fixed in the same fixative overnight, dehydrated and embedded in paraffin. Serial sections were cut at 20 µm thickness for the brain and at 7 µm for the spinal cord. For immunohistochemistry, primary antibodies were used as follows: mouse anti-SMI-32 and mouse anti-SMI-31 (both 1:500, Sternberger Monoclonals); mouse anti-GFAP (1:400, Sigma); goat anti-Glut-1 (1:20, Santa Cruz Biotechnology); rabbit anti-ubiquitin (1/100, Dako) and rabbit anti-albumin (1:250, ICN/Cappel). For motoneuron counts in the spinal cord, SMI-32 positive neurons in the ventral horn were counted bilaterally on 5 equally spaced sections over a distance of 350 µm. To determine the number of motoneurons in the facial nucleus, every $10^{th}$ brain stem section was stained, and all SMI-32 positive neurons in de facial nucleus region counted. This number was multiplied by ten, to estimate the total number of motoneurons in the facial nucleus.

9. Immune Response

Levels of $VEGF_{164}$ in the spinal cord and in the plasma were below the ELISA detection limit (32.5 pg/mL; R&D Systems) in both aCSF and VEGF-treated mice (n=7 for each group). To detect whether there were circulating anti-VEGF antibodies present in VEGF-treated rats, 96-well microtiter plates were coated overnight with 100 µl of a 1 µg/ml solution of $VEGF_{164}$ protein. After incubation with plasma or CSF from aCSF- and VEGF-treated rats, bound anti-$VEGF_{164}$ antibodies were detected by using HRP-labelled anti-rat immunoglobulins (DAKO; 200 ng/ml), the ABC vector staining kit and photospectrometric readout.

10. Statistics

We used SPSS version 10 for all statistical calculations. Cumulative survival statistics were calculated by using Kaplan-Meier statistics. The spontaneous activity, rotarod and weight loss data were analyzed using repeated-measures ANOVA. Student t-tests were used to calculate significant differences for the histological studies.

REFERENCES

1. Przedborski, S., Mitsumoto, H. & Rowland, L. P. Recent advances in amyotrophic lateral sclerosis research. *Curr Neurol Neurosci Rep* 3, 70-7 (2003).
2. Brown, R. H., Jr. & Robberecht, W. Amyotrophic lateral sclerosis: pathogenesis. *Semin Neurol* 21, 131-9 (2001).
3. Rothstein, J. D. Of mice and men: reconciling preclinical ALS mouse studies and human clinical trials. *Ann Neurol* 53, 423-6 (2003).
4. Friedlander, R. M. Apoptosis and caspases in neurodegenerative diseases. *N Engl J Med* 348, 1365-75 (2003).
5. Andersen, P. M. Genetics of sporadic ALS. *Amyotroph Lateral Scler Other Motor Neuron Disord* 2 Suppl 1, S37-41 (2001).
6. Strong, M. & Rosenfeld, J. Amyotrophic lateral sclerosis: a review of current concepts. *Amyotroph Lateral Scler Other Motor Neuron Disord* 4, 136-43 (2003).
7. Cleveland, D. W. & Rothstein, J. D. From Charcot to Lou Gehrig: deciphering selective motor neuron death in ALS. *Nat Rev Neurosci* 2, 806-19. (2001).
8. Gurney, M. E., Pu, H., Chiu, A. Y. et al. Motor neuron degeneration in mice that express a human Cu, Zn superoxide dismutase mutation. *Science* 264, 1772-5 (1994).
9. Howland, D. S., Liu, J., She, Y. et al. Focal loss of the glutamate transporter EAAT2 in a transgenic rat model of SOD1 mutant-mediated amyotrophic lateral sclerosis (ALS). *Proc Natl Acad Sci USA* 99, 1604-9 (2002).
10. Nagai, M., Aoki, M., Miyoshi, I. et al. Rats expressing human cytosolic copper-zinc superoxide dismutase transgenes with amyotrophic lateral sclerosis: associated mutations develop motor neuron disease. *J Neurosci* 21, 9246-54 (2001).
11. Ferrara, N., Gerber, H. P. & LeCouter, J. The biology of VEGF and its receptors. *Nat Med* 9, 669-76 (2003).

12. Carmeliet, P. Angiogenesis in health and disease. *Nat Med* 9, 653-60 (2003).
13. Oosthuyse, B., Moons, L., Storkebaum, E. et al. Deletion of the hypoxia-response element in the vascular endothelial growth factor promoter causes motor neuron degeneration. *Nat Genet* 28, 131-8 (2001).
14. Lambrechts, D., Storkebaum, E., Morimoto, M. et al. VEGF is a modifier of amyotrophic lateral sclerosis in mice and humans and protects motoneurons against ischemic death. *Nat Genet* 34, 383-94 (2003).
15. Storkebaum, E. & Carmeliet, P. VEGF: a critical player in neurodegeneration. *J Clin Invest* 113, 14-8 (2004).
16. Miller, R. G., Mitchell, J. D., Lyon, M. & Moore, D. H. Riluzole for amyotrophic lateral sclerosis (ALS)/motor neuron disease (MND). *Amyotroph Lateral Scler Other Motor Neuron Disord* 4, 191-206 (2003).
17. Acsadi, G., Anguelov, R. A., Yang, H. et al. Increased survival and function of SOD1 mice after glial cell-derived neurotrophic factor gene therapy. *Hum Gene Ther* 13, 1047-59 (2002).
18. Kaspar, B. K., Llado, J., Sherkat, N., Rothstein, J. D. & Gage, F. H. Retrograde viral delivery of IGF-1 prolongs survival in a mouse ALS model. *Science* 301, 839-42 (2003).
19. Ochs, G., Penn, R. D., York, M. et al. A phase I/II trial of recombinant methionyl human brain derived neurotrophic factor administered by intrathecal infusion to patients with amyotrophic lateral sclerosis. *Amyotroph Lateral Scler Other Motor Neuron Disord* 1, 201-6 (2000).
20. Miller, R. G., Petajan, J. H., Bryan, W. W. et al. A placebo-controlled trial of recombinant human ciliary neurotrophic (rhCNTF) factor in amyotrophic lateral sclerosis. rhCNTF ALS Study Group. *Ann Neurol* 39, 256-60 (1996).
21. Lai, E. C., Felice, K. J., Festoff, B. W. et al. Effect of recombinant human insulin-like growth factor-I on progression of ALS. A placebo-controlled study. The North America ALS/IGF-I Study Group. *Neurology* 49, 1621-30 (1997).
22. Borasio, G. D., Robberecht, W., Leigh, P. N. et al. A placebo-controlled trial of insulin-like growth factor-I in amyotrophic lateral sclerosis. European ALS/IGF-I Study Group. *Neurology* 51, 583-6 (1998).
23. Boyd, J. G. & Gordon, T. A dose-dependent facilitation and inhibition of peripheral nerve regeneration by brain-derived neurotrophic factor. *Eur J Neurosci* 15, 613-26 (2002).
24. Raoul, C. & Aebischer, P. ALS, IGF-1 and gene therapy: 'it's never too late to mend'. *Gene Ther* 11, 429-30 (2004).
25. Windebank, A. J. Use of growth factors in the treatment of motor neuron diseases. *Adv Neurol* 68, 229-34 (1995).
26. Masu, Y., Wolf, E., Holtmann, B. et al. Disruption of the CNTF gene results in motor neuron degeneration. *Nature* 365, 27-32 (1993).
27. Giess, R., Holtmann, B., Braga, M. et al. Early onset of severe familial amyotrophic lateral sclerosis with a SOD-1 mutation: potential impact of CNTF as a candidate modifier gene. *Am J Hum Genet* 70, 1277-86 (2002).
28. D'Ercole, A. J., Ye, P. & O'Kusky, J. R. Mutant mouse models of insulin-like growth factor actions in the central nervous system. *Neuropeptides* 36, 209-20 (2002).
29. Gao, W. Q., Shinsky, N., Ingle, G. et al. IGF-I deficient mice show reduced peripheral nerve conduction velocities and decreased axonal diameters and respond to exogenous IGF-I treatment. *J Neurobiol* 39, 142-52 (1999).
30. Ernfors, P., Lee, K. F. & Jaenisch, R. Mice lacking brain-derived neurotrophic factor develop with sensory deficits. *Nature* 368, 147-50 (1994).
31. Moore, M. W., Klein, R. D., Farinas, I. et al. Renal and neuronal abnormalities in mice lacking GDNF. *Nature* 382, 76-9 (1996).
32. Sanchez, M. P., Silos-Santiago, I., Frisen, J. et al. Renal agenesis and the absence of enteric neurons in mice lacking GDNF. *Nature* 382, 70-3 (1996).
33. Orrell, R. W., King, A. W., Lane, R. J. & de Belleroche, J. S. Investigation of a null mutation of the CNTF gene in familial amyotrophic lateral sclerosis. *J Neurol Sci* 132, 126-8 (1995).
34. Azari, M. F., Lopes, E. C., Stubna, C. et al. Behavioural and anatomical effects of systemically administered leukemia inhibitory factor in the SOD1(G93A G1H) mouse model of familial amyotrophic lateral sclerosis. *Brain Res* 982, 92-7 (2003).
35. Feeney, S. J., Austin, L., Bennett, T. M. et al. The effect of leukaemia inhibitory factor on SOD1 G93A murine amyotrophic lateral sclerosis. *Cytokine* 23, 108-18 (2003).
36. Ramer, M. S., Bradbury, E. J., Michael, G. J., Lever, I. J. & McMahon, S. B. Glial cell line-derived neurotrophic factor increases calcitonin gene-related peptide immunoreactivity in sensory and motoneurons in vivo. *Eur J Neurosci* 18, 2713-21 (2003).
37. Luttun, A., Tjwa, M., Moons, L. et al. Revascularization of ischemic tissues by PlGF treatment, and inhibition of tumor angiogenesis, arthritis and atherosclerosis by anti-Flt1. *Nat Med* 8, 831-40 (2002).
38. Thorne, R. G. & Frey, W. H., 2nd. Delivery of neurotrophic factors to the central nervous system: pharmacokinetic considerations. *Clin Pharmacokinet* 40, 907-46 (2001).
39. Yamaguchi, S., Iwata, K. & Shibuya, M. Soluble Flt-1 (soluble VEGFR-1), a potent natural antiangiogenic molecule in mammals, is phylogenetically conserved in avians. *Biochem Biophys Res Commun* 291, 554-9 (2002).
40. Luttun, A., Autiero, M., Tjwa, M. & Carmeliet, P. Genetic dissection of tumor angiogenesis: are PlGF and VEGFR-1 novel anti-cancer targets? *Biochim Biophys Acta* 1654, 79-94 (2004).
41. Stockhammer, G., Poewe, W., Burgstaller, S. et al. Vascular endothelial growth factor in CSF: a biological marker for carcinomatous meningitis. *Neurology* 54, 1670-6 (2000).
42. Marti, H. H. & Risau, W. Systemic hypoxia changes the organ-specific distribution of vascular endothelial growth factor and its receptors. *Proc Natl Acad Sci USA* 95, 15809-14 (1998).
43. Nutt, J. G., Burchiel, K. J., Comella, C. L. et al. Randomized, double-blind trial of glial cell line-derived neurotrophic factor (GDNF) in PD. *Neurology* 60, 69-73 (2003).
44. Veldink, J. H., Bar, P. R., Joosten, E. A. et al. Sexual differences in onset of disease and response to exercise in a transgenic model of ALS. *Neuromuscul Disord* 13, 737-43 (2003).
45. Lino, M. M., Schneider, C. & Caroni, P. Accumulation of SOD1 mutants in postnatal motoneurons does not cause motoneuron pathology or motoneuron disease. *J Neurosci* 22, 4825-32 (2002).
46. Autiero, M., Waltenberger, J., Communi, D. et al. Role of PlGF in the intra- and intermolecular cross talk between the VEGF receptors Flt1 and Flk1. *Nat. Med* 9, 936-43 (2003).
47. Airaksinen, M. S. & Saarma, M. The GDNF family: signalling, biological functions and therapeutic value. *Nat Rev Neurosci* 3, 383-94 (2002).

48. Jin, K., Zhu, Y., Sun, Y. et al. Vascular endothelial growth factor (VEGF) stimulates neurogenesis in vitro and in vivo. *Proc Natl Acad Sci USA* 99, 11946-50 (2002).
49. Pepper, M. S., Ferrara, N., Orci, L. & Montesano, R. Leukemia inhibitory factor (LIF) inhibits angiogenesis in vitro. *J Cell Sci* 108 (Pt 1), 73-83 (1995).
50. Ruprecht, K., Stadelmann, C., Hummel, V. et al. Brain derived neurotrophic factor does not act on adult human cerebral endothelial cells. *Neurosci Lett* 330, 175-8 (2002).
51. Koh, S. W. Ciliary neurotrophic factor released by corneal endothelium surviving oxidative stress ex vivo. *Invest Opthalmol Vis Sci* 43, 2887-96 (2002).
52. Louissaint, A., Jr., Rao, S., Leventhal, C. & Goldman, S. A. Coordinated interaction of neurogenesis and angiogenesis in the adult songbird brain. *Neuron* 34, 945-60 (2002).
53. Weston, G. C., Haviv, I. & Rogers, P. A. Microarray analysis of VEGF-responsive genes in myometrial endothelial cells. *Mol Hum Reprod* 8, 855-63 (2002).
54. Giess, R., Beck, M., Goetz, R. et al. Potential role of LIF as a modifier gene in the pathogenesis of amyotrophic lateral sclerosis. *Neurology* 54, 1003-5 (2000).
55. Storment, J. M., Meyer, M. & Osol, G. Estrogen augments the vasodilatory effects of vascular endothelial growth factor in the uterine circulation of the rat. *Am J Obstet Gynecol* 183, 449-53 (2000).
56. Lissbrant, I. F., Hammarsten, P., Lissbrant, E. et al. Neutralizing VEGF bioactivity with a soluble chimeric VEGF-receptor protein flt(1-3)IgG inhibits testosterone-stimulated prostate growth in castrated mice. *Prostate* 58, 57-65 (2004).
57. Tsuzuki, Y., Fukumura, D., Oosthuyse, B. et al. Vascular endothelial growth factor (VEGF) modulation by targeting hypoxia-inducible factor-1 alpha→hypoxia response element→VEGF cascade differentially regulates vascular response and growth rate in tumors. *Cancer Res* 60, 6248-52 (2000).
58. Krum, J. M., Mani, N. & Rosenstein, J. M. Angiogenic and astroglial responses to vascular endothelial growth factor administration in adult rat brain. *Neuroscience* 110, 589-604 (2002).
59. Caroni, P., Schneider, C., Kiefer, M. C. & Zapf, J. Role of muscle insulin-like growth factors in nerve sprouting: suppression of terminal sprouting in paralyzed muscle by IGF-binding protein 4. *J Cell Biol* 125, 893-902 (1994).
60. Kunst, C. B., Messer, L., Gordon, J., Haines, J. & Patterson, D. Genetic mapping of a mouse modifier gene that can prevent ALS onset. *Genomics* 70, 181-9 (2000).

The invention claimed is:

1. A method for treating amyotrophic lateral sclerosis (ALS) or enhancing the survival of a motor neuron in a subject diagnosed with a motoneuron disease, said method comprising:

administration of a vascular endothelial growth factor-A ("VEGF-A") protein into the cerebrospinal fluid of the subject at a dose within a range of 0.05 μg/kg/day and 1 μg/kg/day of the subject's body mass, wherein the VEGF-A protein is selected from the group consisting of: $VEGF_{121}$, $VEGF_{145}$, and $VEGF_{165}$, and $VEGF_{189}$, thus treating the ALS disease or enhancing the survival of a motor neuron in the subject diagnosed with a motoneuron disease.

2. The method according to claim 1 wherein said dose is administered within a range of 0.2 μg/kg/day and 0.8 μg/kg/day.

3. The method according to claim 1 wherein said administration is intrathecal.

4. The method according to claim 1 wherein said administration is intracerebroventricular.

5. The method according to claim 1 wherein said continuous administration of VEGF occurs via an implanted osmotic mini-pump.

6. A method for treating amyotrophic lateral sclerosis (ALS) or enhancing the survival of a motor neuron in a subject diagnosed with a motoneuron disease, the method comprising:

administering a vascular endothelial growth factor ("VEGF") protein to the subject at a dosage range of between 0.05 μg/kg/day and 1 μg/kg/day of the subject's body mass, wherein the VEGF protein is selected from the group consisting of $VEGF_{121}$, $VEGF_{145}$, and $VEGF_{165}$, and $VEGF_{189}$, and wherein the administration is intrathecal or intracerebroventricular, thus treating the ALS disease or enhancing the survival of a motor neuron in the subject diagnosed with a motoneuron disease.

7. A method for treating amyotrophic lateral sclerosis (ALS) or enhancing the survival of a motor neuron in a subject diagnosed with a motoneuron disease, the method comprising:

administering a vascular endothelial growth factor ("VEGF") protein into the cerebrospinal fluid of the subject at a dosage range of between 0.05 μg/kg/day and 1 μg/kg/day of the subject's body mass, wherein the VEGF protein is selected from the group consisting of $VEGF_{121}$, $VEGF_{145}$, and $VEGF_{165}$, and $VEGF_{189}$, thus treating the ALS disease or enhancing the survival of a motor neuron in the subject diagnosed with a motoneuron disease.

* * * * *